(12) United States Patent
Halaka

(10) Patent No.: US 7,981,080 B2
(45) Date of Patent: Jul. 19, 2011

(54) SKIN COOLING APPARATUS AND METHOD

(76) Inventor: Folim G. Halaka, Lake Forest, IL (US)

( * ) Notice: Subject to any disclaimer, the term of this patent is extended or adjusted under 35 U.S.C. 154(b) by 211 days.

(21) Appl. No.: 12/319,437

(22) Filed: Jan. 7, 2009

(65) Prior Publication Data
US 2010/0174237 A1 Jul. 8, 2010

(51) Int. Cl.
*A61F 7/12* (2006.01)
(52) U.S. Cl. .................................................. 604/114
(58) Field of Classification Search .................. 604/114
See application file for complete search history.

(56) References Cited

U.S. PATENT DOCUMENTS

| | | | | |
|---|---|---|---|---|
| 4,440,167 A | * | 4/1984 | Takehisa | 606/20 |
| 5,578,014 A | * | 11/1996 | Erez et al. | 604/192 |

* cited by examiner

*Primary Examiner* — Nicholas D Lucchesi
*Assistant Examiner* — Jason Flick
(74) *Attorney, Agent, or Firm* — Olson & Cepuritis, Ltd.

(57) ABSTRACT

Skin cooling apparatus is provided for use with a medical treatment device such as a hypodermic syringe or a skin ablation laser or other electromagnetic source. The skin cooling apparatus provides selective, localized cooling of the target area that is acted upon by the medical treatment device. Included is a support body engaging at least a portion of the medical treatment device, for supporting and orienting the medical treatment device to the target area. A solid state cooling device such as a thermoelectric or Peltier device is carried by the support body and includes a cooling surface facing the target area of a patient's skin surface. The support body may be flexible so as to allow the medical treatment device to be inclined relative to the skin surface. The support body may also include aiming structure for directing the medical treatment device to a particular point within the target area.

2 Claims, 7 Drawing Sheets

SKIN COOLING APPARATUS AND METHOD

FIELD OF THE INVENTION

The present invention pertains to the cooling of skin surface portions, to alleviate pain associated with medical treatment applied to the skin. The present invention also relates to apparatus and method to perform cooling of skin surface portions to which a medical treatment device is applied.

BACKGROUND OF THE INVENTION

Nerve endings in the skin layers are particularly sensitive to medical treatments that interact with the patient's skin. These types of medical treatments include, for example, hypodermic injections and skin ablation, especially using powerful laser ablation devices. No matter how necessary the medical treatment, the associated levels of pain can be great enough to not only cause patient discomfort, but to mandate that pain relief in some form be provided. It is of course preferable to avoid using pain relieving drugs such as Novocaine, whenever possible. Accordingly, different types of pain relieving devices have been explored. Cooling of the skin has been observed to lessen pain associated with hypodermic injections. As reported in a JAMA research letter entitled "Pain Associated with Injection Using Frozen Versus Room-Temperature Needles," K. Denkler, Oct. 3, 2001, the use of ice-cold needles have been found to minimize injection pain in procedures that require several needle sticks for each area to be treated.

The cooling of a patient's skin to lessen the pain of hypodermic injections is also described in several U.S. patents. For example, U.S. Pat. No. 4,725,265—Sairenji places a cooling gas injection nozzle adjacent a syringe-mounted hypodermic needle. In addition to the cooling gas injection nozzle, a source of cooling gas in the form of a cooling gas cylinder may be mounted to the barrel of the hypodermic syringe. Accordingly, two external assemblies are required to be secured to the outside of the syringe barrel, thus rendering the syringe assembly cumbersome and difficult to operate.

U.S. Pat. No. 5,236,419—Seney discloses a hypodermic syringe assembly in which a syringe barrel is disposed within an outside support which extends beyond a needle attached to the syringe. Extending from the support is a canister that is filled with a thermal energy storage solution. The support surrounds the hypodermic needle and extends beyond the needle, toward the patient's skin. A hole in the support allows the hypodermic needle to contact the patient's skin when the hypodermic needle and syringe barrel are slidably advanced along the support. Prior to use, the syringe and canister assembly are put in a freezer at a temperature as low as 0 degrees Fahrenheit for approximately an hour. After removal from the freezer, the syringe assembly is effective for use for a minimum of three minutes during which time the canister is pressed against the skin where injection is to occur and is held against the skin for a time period ranging between ten to thirty seconds. In addition to requiring external freezer apparatus, the syringe arrangement is effective only for a relatively short time, requiring that the injection be given in close proximity to the freezing apparatus.

U.S. Pat. No. 3,605,742—Tibbs provides a relatively massive mechanism for operating a hypodermic syringe. Included is a plunger operating mechanism including a spring-loaded piston. A container of pressurized, highly volatile cooling liquid such as a fluorinated or chlorinated hydrocarbon, is mounted along side the mechanism which holds and operates the syringe. The pressurized coolant is released adjacent the hypodermic needle so as to surround the needle tip while contacting the patient's skin. The mechanism increases the size and weight of the syringe at least several times over, and renders the combination unsuitable for many applications where pressurized gas is not available and/or a bulky hypodermic injecting device is unsuitable.

U.S. Pat. No. 5,578,014—Erez et al. also discloses a relatively massive, bulky hypodermic injecting arrangement. Included is a holder for a hypodermic syringe joined to an adjacent forced air cooling system in which a fan cools a heat sink attached to a cooling plate. The cooling plate is located between the hypodermic needle and the patient's skin and includes a central passageway allowing the hypodermic needle to contact the patient's skin. The syringe is mounted for movement along a guide rod which orients the hypodermic needle with the central passageway of the cooling plate. The cooling plate first contacts the patient's skin and after a sufficient time has elapsed, the hypodermic syringe is advanced through a hole in the cooling plate, bringing the hypodermic needle in contact with the patient's skin. The entire mechanism increases the size and mass of the hypodermic syringe several times, rendering the device unsuitable where a portable, light weight hypodermic injection system is required.

U.S. Patent Application No. 2005/0182364 A1 discloses a cooling device utilizing ice as the cooling source. The device is provided for relieving pain associated with hypodermic injections, with the device being separate from the hypodermic syringe. A quantity of water is disposed within a hollow body that includes a retaining rod disposed within the water, and a removable cover for containing the water in contact with the retaining rod. Upon freezing, the water is converted to ice that adheres to the retaining rod, allowing the cover to be removed, thereby exposing the ice for contact to the patient's skin. After use, the device is discarded. Thus, external freezing apparatus is required to convert the water to a solid piece of ice, rendering the device unsuitable for applications where freezing apparatus is not available.

SUMMARY OF THE INVENTION

The present invention provides a novel and improved self-contained skin cooling apparatus and method that minimizes disadvantages associated with the prior art devices and provides advantages in construction, mode of operation and use.

In one embodiment, skin cooling apparatus is provided for use with a medical treatment device that interacts with a target area of a patient's skin surface. The skin cooling apparatus provides selective, localized cooling of the target area and includes a support body engaging at least a portion of the medical treatment device and to orient the medical treatment device with respect to the target area. The support body includes a distal end adjacent the target area and a proximal end remote from the target area. A solid state cooling device is carried adjacent the distal end of the support body and includes an exposed cooling surface facing the target area. Examples of medical treatment devices include a hypodermic syringe having a barrel engaged with the support body and a conductor or waveguide such as an optic fiber cable for conducting output of an electromagnetic radiation source such as an ablation laser, to the target area.

In one example, the skin cooling apparatus includes an aiming structure formed with the support body for aiming the medical treatment device with respect to the target area. The aiming structure can include a wall of the support body that defines an aperture through which the medical treatment device interacts with a patient's skin surface. In another example, the support body is flexible so as to allow the medical treatment device to be positioned at an angle to the skin surface.

The present invention also provides a method of selective, localized cooling of the target area of a patient's skin. The method is employed in conjunction with a medical treatment device that interacts with the target area. The method includes engaging at least a portion of the medical treatment device so as to orient the medical treatment device to the target area. A solid state cooling device such as a thermoelectric heat pump chills a cooling surface of the solid state cooling device when the device is electrically energized. The solid state cooling device is carried by the distal end of the support body, with the cooling surface facing the target area. At least a portion of the target area is contacted with the cooling surface, and the solid state cooling device is energized so as to provide cooling to the target area.

In one example, the method further includes providing the support body with a flexible portion and flexing the support body so as to dispose the medical treatment device at an angle to the skin surface of the target area.

DESCRIPTION OF THE PREFERRED EMBODIMENTS

Figure 1:
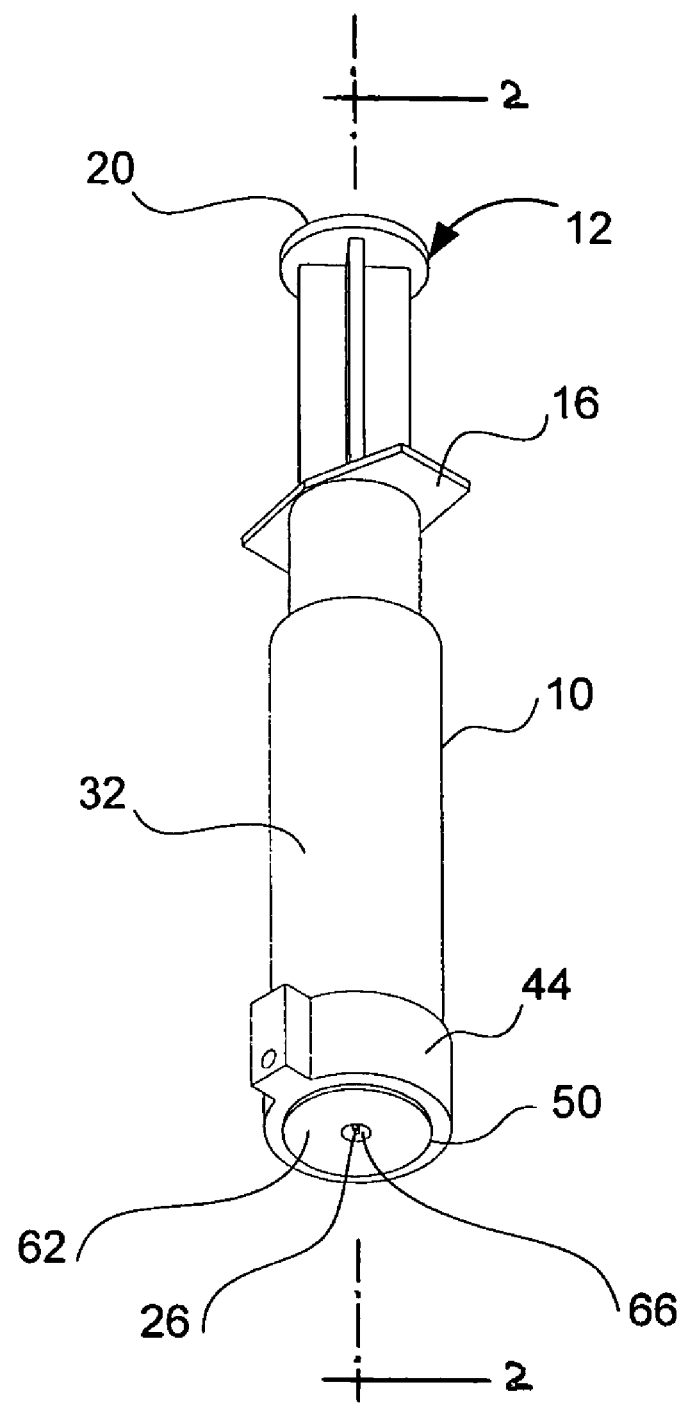
FIG. 1 is a perspective schematic representation of skin cooling apparatus associated with a hypodermic syringe.

The invention disclosed herein is, of course, susceptible of embodiment in many different forms. Shown in the drawings and described herein below in detail are preferred embodiments of the invention. It is understood, however, that the present disclosure is an exemplification of the principles of the invention and does not limit the invention to the illustrated embodiments. For ease of description, skin cooling apparatus embodying the present invention is described herein below in a usual assembled position as shown in the accompanying drawings, and terms such as upper, lower, horizontal, longitudinal, proximal, distal, etc., may be used herein with reference to this usual position. However, the skin cooling apparatus may be manufactured, transported, sold or used in orientations other than that described and shown herein.

Figure 2:
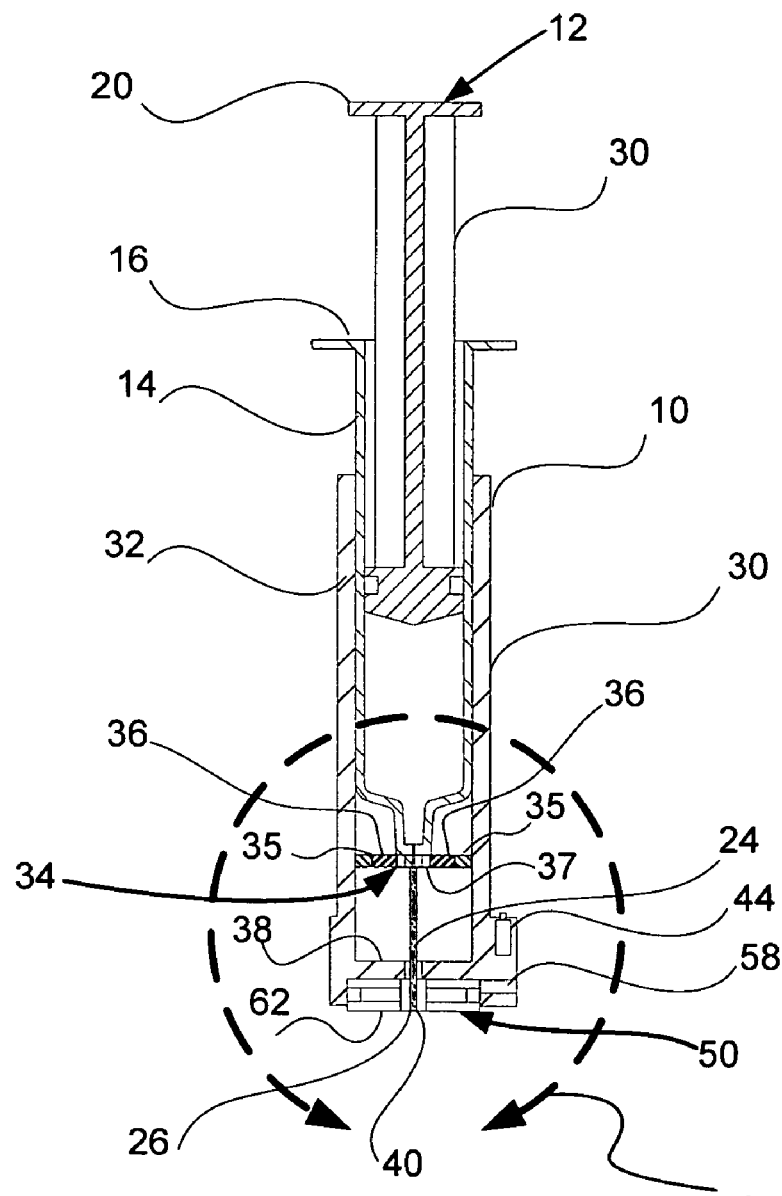
FIG. 2 is cross-sectional view taken along the plane 2-2 of FIG. 1.
Figure 3:
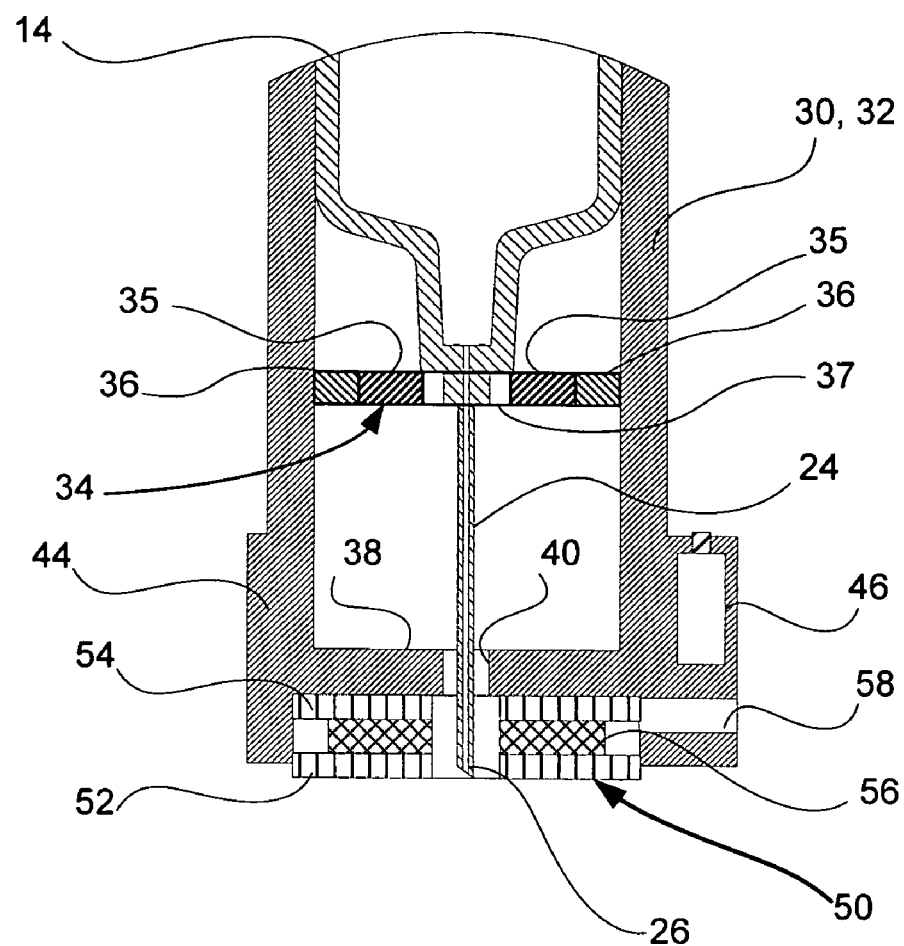
FIG. 3 shows a portion of FIG. 2 taken on an enlarged scale.

Referring now to FIGS. 1-3, skin cooling apparatus generally indicated at 10 is shown associated with a hypodermic syringe generally indicated at 12. Hypodermic syringe 12 may take different forms, but preferably is of conventional construction; including a syringe barrel 14 having operating lugs 16 and a plunger 18 having an operating end 20. As can be seen in FIGS. 2 and 3, hypodermic syringe 12 further includes a hypodermic injection needle 24 having a skin piercing tip 26.

Referring again to FIGS. 1-3, syringe barrel 14 is mounted within support body 30. Preferably, support body 30 is in the form of a hollow tube having an end wall 58. Support body 30 can be made of virtually any metal, plastic or composite material, but is preferably made from conventional light weight plastic material. As indicated in the Figures, it is generally preferred that barrel 14 form a close fit with the interior of support body 30 but can be slidably received therewithin. In a preferred embodiment, barrel 14 is mounted for translation within support body 30 in the downward direction illustrated in FIGS. 1-3. It is generally preferred that the interior bore of support body 30 is provided with an abutment such as stop member 34 to limit travel of the syringe barrel 14 within the support body 30 and thus limit the extension of hypodermic needle 24 beyond cooling apparatus 10, thereby limiting the depth of penetration of the hypodermic needle in the patient's skin to a predetermined depth. Stop member 34 preferably has a rigid portion 35 and a flexible portion 36 that defines center hole 37 to accommodate the hypodermic syringe needle 24. The syringe barrel 14 is positioned to rest on the inner edge of the flexible portion 36 and prevent the hypodermic syringe needle 24 from projecting beyond cooling apparatus 10. When the hypodermic syringe is to be used, syringe barrel 14 is translated downwardly until it rests against the rigid portion 35 of the stop member 34. The rigid portion 35 can be of any relatively stiff plastic, metal, or ceramic, and preferably is made from plastic such as polycarbonate, polystyrene, acrylic, and the like. The flexible member 36 can be of any flexible polymeric material, and preferably from an elastic, elastomeric or thermoelastic material with a Shore Durometer value of about 15 to about 100, preferably about 25 to about 45 on Durometer Scale A, as described in ASTM d2240-00.

By selecting appropriate position of stop member 34 within the bore of syringe barrel 14 the travel of hypodermic needle 24 can be adjusted to deliver medication within a particular skin layer or below, e.g., to the dermis as well as into subcutaneous tissues. If desired, the plunger and/or syringe barrel may be suspended or otherwise controlled by springs or other bias members.

Referring to FIGS. 2 and 3, support body 30 includes a bottom end wall 38 defining a central aperture 40 for receiving and aiming hypodermic needle 24 at the desired portion of the target area of the patient's skin surface. If desired, the end wall 38 can be omitted, with aiming of the hypodermic needle being provided by other structure as will be described herein.

In a preferred embodiment, support body 30 includes a first, generally cylindrical portion 32 having a bore sized to slidably receive syringe barrel 14, and an enlarged band 44 located at the bottom end of the support body. As can be seen, for example, in FIG. 3, the inner bore of band 44 is larger than the inner bore of cylindrical portion 32, thereby allowing band 44 to accommodate components of enlarged size. End wall 58 in band 44 receives a solid state cooling device generally indicated at 50. With additional reference to FIGS. 4-6, solid state cooling device 50 has a generally circular or round disk shape with a thickness that is relatively small compared to the device diameter. In the preferred embodiment, the solid state cooling device 50 preferably comprises a thermoelectric device. Solid state cooling device 50 preferably comprises a class of thermoelectric devices exhibiting the Peltier effect, in which a device operates as a thermoelectric heat pump, transferring heat from one side of the device to the other, with the direction of heat transfer being controlled by the polarity of the voltage applied to the device. Although a round disc is shown in the illustrated embodiments, solid state cooling device 50 may take virtually any shape as may be desired, such as a square disc.

In the preferred embodiment, the solid state cooling device 50 includes a cooling plate 52 at its bottom side and a warming plate 54 at its top side. Disposed between plates 52, 54 is a layer 56 of semiconductor material arranged with spaced apart portions of "P" type semiconductor and "N" type semiconductor material. By applying an external voltage from a direct current power source, charge carriers are made to flow through the "P" type and "N" type semiconductors, giving rise to the Peltier effect, with the polarity of the power source being selected such that cooling is provided at plate 52 while heating is provided at plate 54. Preferably, end wall 58 of support body 30 is made of a heat conductive material with thermal mass sufficient to absorb heat accumulated at warming plate 54. Additionally, forced air provided by a fan or the like forced air source may be used to remove accumulated heat.

Figure 4:
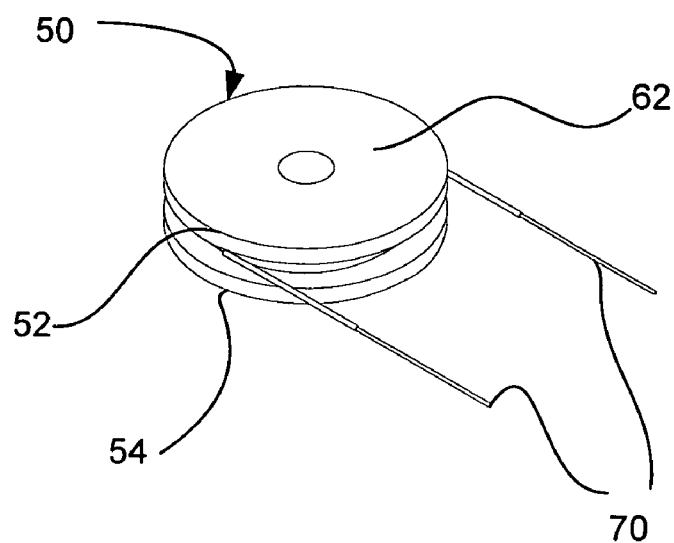
FIG. 4 is a perspective view of the solid state cooling device used with the skin cooling apparatus.
Figure 5:
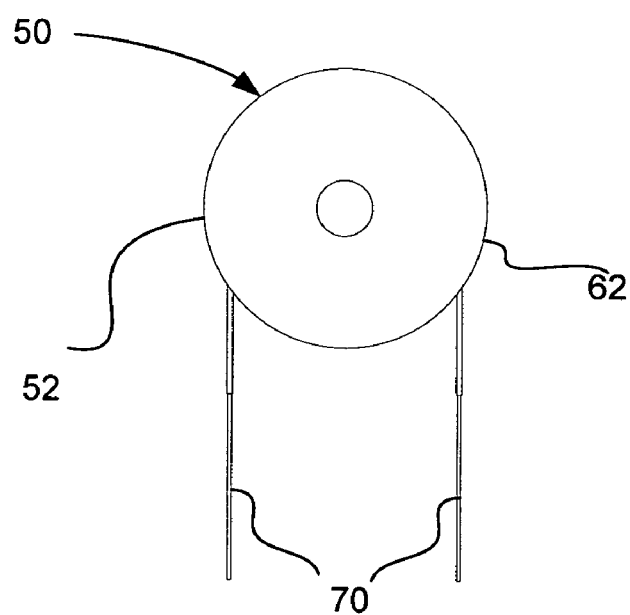
FIG. 5 is a front elevational view thereof.
Figure 6:
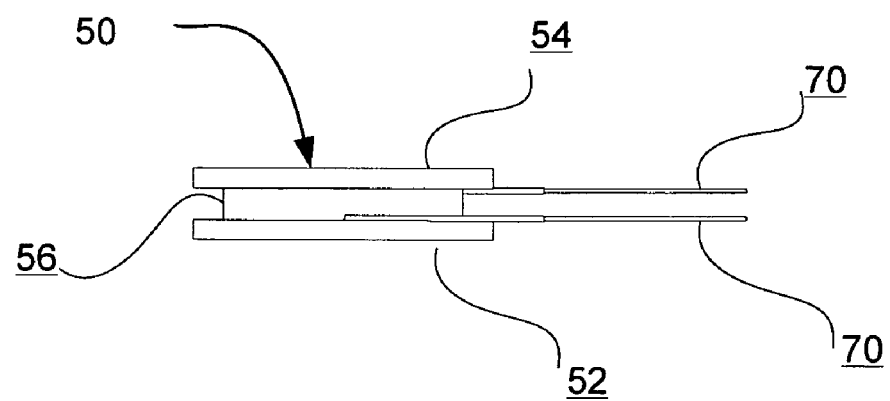
FIG. 6 is side elevational view thereof.

With reference to FIGS. 4-6, solid state cooling device 50 is shown with electrical leads 70 for connection to a power source (not shown) to be applied to the layer 56 of solid state material in a known manner. Electrical connection can be made to an external source with an electrical plug 58 being provided in band 44. Alternatively, power can be provided by small sized storage batteries contained in a housing 46 that is formed as a protrusion of band 44. Output from the batteries is electrically coupled to the semiconductor layer 56 in a known manner.

The bottom exposed surface 62 of plate 52 is the cold surface presented to the patient's skin to provide cooling for the designated target area. Preferably, the solid state cooling device has a diameter (or alternatively a width if non-circular) ranging between 0.1 and 10 centimeters and most preferably ranging between 1 and 3 centimeters. The height of the solid state cooling device ranges between 0.1 and 10 centimeters, and preferably ranges between 0.2 and 1 centimeter. Preferably, cooling power for the solid state cooling device ranges between 1 and 100 watts and most preferably between 5 and 20 watts.

In one example, the solid state cooling device preferably comprises a round module with center hole commercially available from TE Technology Inc. of Traverse City, Mich., and commercially available as either Product No. CH-19-1.0-1.3 or Product No. CH-38-1.0-0.8. The smaller of these two products has an outside diameter of 15 millimeters, an internal or central diameter of 3 millimeters and a height of 3.6 millimeters. With the application of 3.6 amps direct current, the cooling device produces 5.2 watts of cooling power.

Referring to FIG. 3, as mentioned, end wall 38 of support body 30 has an internal aperture 40 allowing passage of hypodermic needle 24 therethrough. In order to contact the skin surface of the patient, the solid state cooling device 50 is also provided with a central bore 66, aligned with central bore 40 of end wall 38. In the embodiment shown in FIGS. 1-3, the central bores 40, 66 preferably are coaxial and are defined by generally cylindrical internal walls. Accordingly, as indicated in FIG. 1 and other Figures, the tip 26 of hypodermic needle 24 is free to clear the skin cooling apparatus so as to interact with the patient's skin surface.

In use, the skin cooling apparatus 10 and hypodermic syringe 12 cooperate to provide improved treatment, lessening discomfort to the patient. Initially, the surface 62 of cooling plate 52 is placed in contact with the target area of the patient's skin surface to be treated. After a sufficient amount of time to allow heat energy to be absorbed from the patient's skin to solid state cooling device 50, numbing of the patient's skin occurs. The hypodermic syringe is then urged downwardly by downward pressure on operating lugs 16 of syringe barrel 14, causing the syringe barrel to slide within the cylindrical portion 32 of support body 30. During this initial activation period, the hypodermic needle 24 is guided toward the target area by cylindrical portion 32. With continued pressure on operating lugs 16, the syringe barrel 14 is brought to the position indicated in FIG. 3, where the hypodermic needle 24 enters through apertures 40, 66 so as to reach the cooling surface 62 of solid state cooling device 50. The apertures 40, 66 and the interior walls forming those apertures act to provide a further aiming of hypodermic needle 24 to ensure accurate positioning of the hypodermic needle tip 26 within the target area, already prepared by the solid state cooling device 50.

Preferably, one or more stop members 34 are positioned within the internal bore wall of cylindrical portion 32, so as to interfere with syringe barrel 14. It is generally preferred that the stop members 34 be positioned so as to define a desired amount of penetration of the hypodermic needle tip 26 within the patient's body. The stop member 34 may be provided as one or more protrusions disposed about the interior of cylindrical portion 32. Alternatively, the stop member can comprise one or more arcuate segments or alternatively an annulus or ring protruding from the interior bore wall of cylindrical portion 32 of support body 30. If desired, the stop member 34 can be made resilient so as to interfere with normal pressure applied to operating lugs 16, but which can be overcome with additional applied force to achieve a deeper penetration of hypodermic needle tip 26 within the patient's body, as may be desired.

The solid state cooling device 50 is energized by applying electrical voltage to the solid state cooling device 50 such that heat energy is transferred from cooling plate 52 to warming plate 54. The solid state cooling device 50 cools the surface of the patient's skin over a localized targeted area. Cooling such as that carried out according to the Peltier effect is initiated by energizing the solid state cooling device with one or more appropriate electrical signals. Electrical energization of the solid state cooling device continues until the desired numbing effect is observed.

Energization of the solid state cooling device may be uncontrolled or, alternatively, a control system (not shown) may be employed to achieve a desired temperature or heat flow at the cooling face 62. For example, the energization to the solid state cooling device may be interrupted for a controlled amount of time to prevent further lowering of the temperature of the cooling surface 62. The current may, for example, be interrupted using a resistance temperature detector (RTD) device, as is known. Alternatively, the polarity of the energization applied to the solid state cooling device may be reversed so as to momentarily reverse the direction of heat flow across the solid state device. As a further alternative, parameters of the electrical signal applied to the solid state cooling device may be modified by the miniaturized electronic components and circuitry as are known in the art, to control the temperature and/or heat flow associated with the solid state cooling device.

Figure 8:
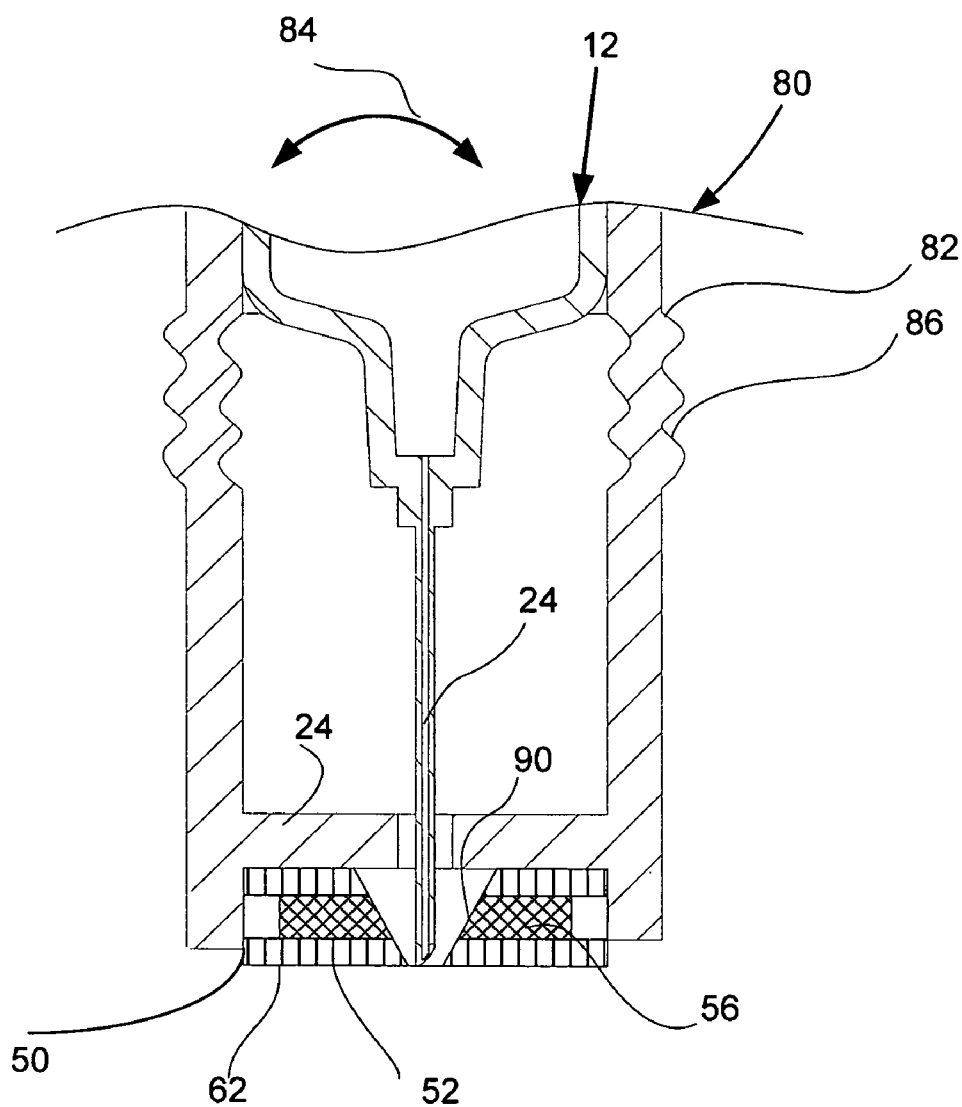
FIG. 8 is a cross-sectional view similar to that of FIG. 3 but showing an alternative, flexible skin cooling apparatus.

Referring now to FIG. 8, an alternative embodiment of skin cooling apparatus is generally indicated at 80. The skin cooling apparatus 80 is similar to the aforedescribed skin cooling apparatus 10, except that the support body 82 is flexible or bendable, allowing the longitudinal axis of the hypodermic syringe 12 to be pivoted as indicated by arrow 84. The support body 82 may be rendered flexible or bendable by employing flexible or bendable material such as plastic or rubber. As an alternative to using relatively pliant, resiliently deformable material, a stiffer material can be used with a pleated section or boot, such as pleated section 86 shown in FIG. 8. While a resiliently pliable material for the support body will render the hypodermic syringe 12 stable and will guide the direction of the hypodermic syringe relative to the target area, the introduction of a pleated section such as pleated section 86 will provide an enhanced guidance of hypodermic syringe 12 and an enhanced aiming of hypodermic needle 24. In the preferred embodiment, pleated portion 86 is integrally formed with the remainder of support body 82, and is preferably comprised of a flexible material such as polypropylene, polyethylene, and the like. Alternatively, the pleated portion can be formed separately and later joined to the remaining portions of support body 82.

If desired, the hypodermic syringe 12 can fixedly engage support body 82 so as to preclude translation movement of the hypodermic syringe with respect to the support body. In this type of alternative arrangement, the translation motion of the hypodermic syringe needed to advance the hypodermic needle 24 to enter the target area of the skin surface is provided by the relatively easy compression of pleated portion 86, allowing the hypodermic needle 24 to penetrate beyond the cooling surface 62 of solid state cooling device 50.

Referring again to FIG. 8, support body 82 extends to surround solid state cooling device 50, so as to rigidly secure the position of the solid state cooling device with respect to the bottom end of support body 82. If desired, the straight bore aperture 66 extending through cooling device 50, as shown in FIG. 3, may be employed in the arrangement of FIG. 8. However, if greater control of the aiming of hypodermic needle 24 is desired, solid state cooling device 50 may be provided with a generally conical bore 90, as shown in FIG. 8. The conical bore 90 provides a smaller exit aperture at the cooling surface 62, while allowing the hypodermic needle a wide range of motion, thus providing a greater degree of aiming control over the hypodermic needle 24, during operation of the hypodermic syringe.

In FIG. 8, the electrical leads needed to energize the solid state cooling device are omitted for clarity of illustration. If desired, the electrical leads can extend to an external power supply or alternatively, could extend to one or more electrical batteries carried on support body 82.

Figure 7:
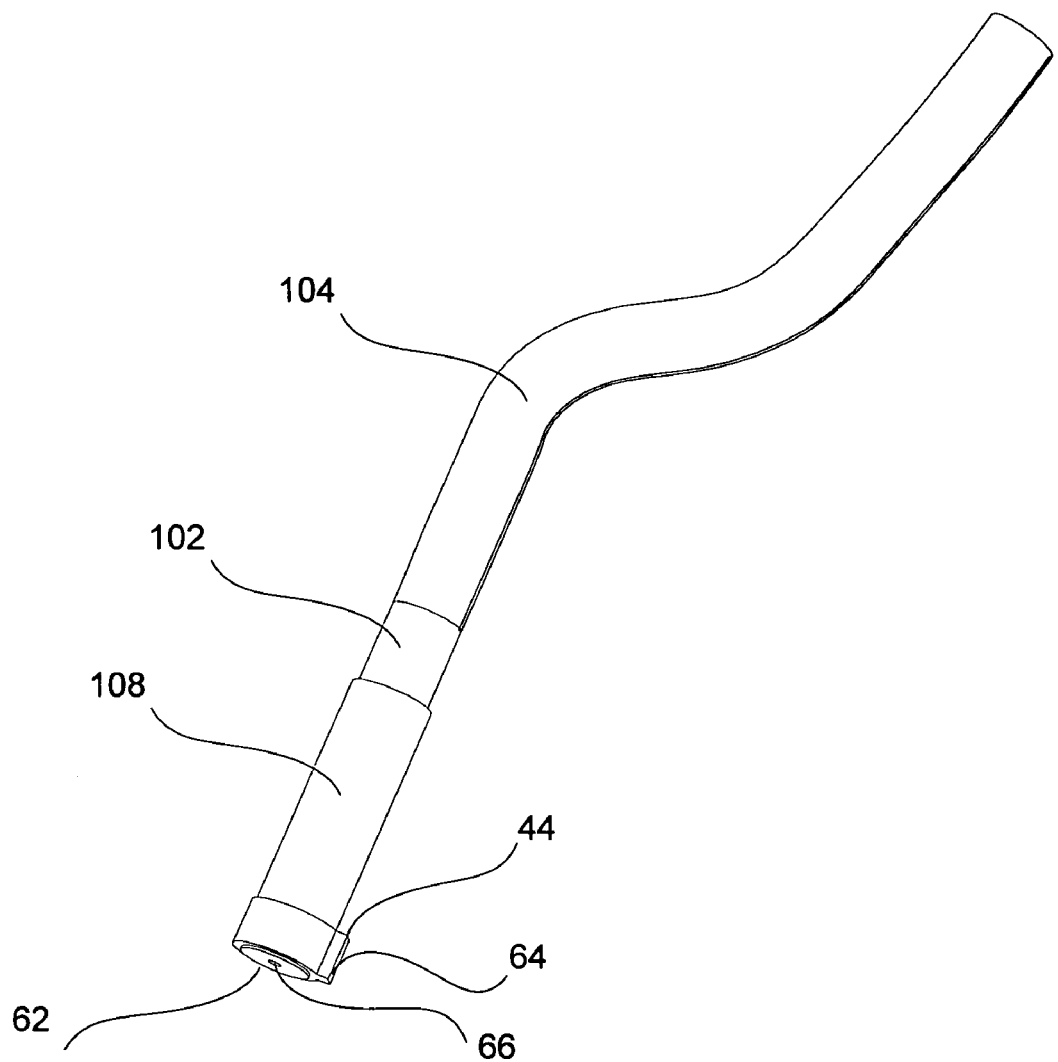
FIG. 7 is a schematic perspective view of skin cooling apparatus associated with an optic fiber cable for delivering laser ablation energy to the target area of a patient's skin surface.

Referring now to FIG. 7, skin cooling apparatus generally indicated at 100 is utilized with a medical treatment device for delivering thermal energy to a patient's skin surface. In the preferred embodiment, a conductor 102, preferably in the form of an optic fiber cable, is connected to the output of an electromagnetic radiation source (not shown). In the preferred embodiment, the conductor or waveguide 102 is disposed within an outer cable sheath 104. Skin cooling apparatus 100 includes a support body 108 that receives conductor 102 and provides aiming of the output of conductor 102 to a desired point in the target area of the patient's skin surface. A band 44 with an optional battery compartment 46 is located adjacent the free end of support body 108. The cooling surface 62, visible in FIG. 7 forms part of a solid state cooling device of the type described above. A central aperture 66 formed in the solid state cooling device allows electromagnetic radiation to exit the free end of conductor 102 disposed adjacent the solid state cooling device. If desired, the radiation beam may be focused using one or more lenses, suitable for the purpose, as is known. The lenses may be contained within band 44 or within support body 108. In either event, the support body 108 provides aiming of the conductor 102 and the electromagnetic radiation output therefrom.

Preferably, electromagnetic radiation is controlled by the operator at a point remote from the skin cooling apparatus. However, if desired, one or more controls for the electromagnetic radiation device may conveniently be provided for attachment to support body 108. One or more controls for the power source for the solid state cooling device may also be located on or near support body 108.

In use, the solid state cooling device is electrically energized so as to provide cooling at surface 62, placed in contact with the patient's skin. After a suitable amount of time has passed to allow the target area of the patient's skin surface to become numb, output from the electromagnetic radiation source is passed through conductor 102 and aperture 66 so as to apply thermal energy to the patient's skin. Any of a variety of electromagnetic radiation sources may be used. For example, the electromagnetic radiation source may comprise a laser operating in the near infrared frequency range or alternatively may be a collimated non-coherent light source. Medical treatment applied to the patient's skin may comprise skin ablation, for example.

The foregoing description and the accompanying drawings are illustrative of the present invention. Still other variations and arrangements of parts are possible without departing from the spirit and scope of this invention.

I claim:

1. Skin cooling apparatus for use with a hypodermic syringe that interacts with a target area of a patient's skin surface for selective, localized cooling of the target area, the hypodermic syringe having a barrel and a needle attached to the barrel, the skin cooling apparatus comprising:

a flexible, tubular support body engaging at least a portion of the barrel of the hypodermic syringe for orienting the needle to the target area;

the support body having a distal end adjacent the target area and a proximal end remote from the target area; and a solid state cooling device adjacent the distal end of the support body and surrounded by the support body, including an exposed cooling surface for direct contact with the target area and defining a hole through which the needle is aimed at the target area; wherein the support body is pivotable for needle orientation at different angles to the skin surface of the target area and the hole is a conical hole through which the needle is aimed at the target area, the conical hole having a relatively smaller needle exit aperture at the cooling surface than a needle entrance aperture into the cooling device.

2. The skin cooling apparatus of claim 1, wherein the support body includes a bellows portion for orienting the needle.

* * * * *